United States Patent

Gänsler et al.

[11] Patent Number: 5,891,050
[45] Date of Patent: Apr. 6, 1999

[54] METHOD AND DEVICE FOR DETERMINING AND MONITORING THE DEGREE OF NARCOSIS IN HUMANS

[75] Inventors: Tomas Gänsler, Lund; Maria Hansson, Lomma, both of Sweden

[73] Assignee: SCS Medicinproject Aktiebolag, Stockholm, Sweden

[21] Appl. No.: 930,260

[22] PCT Filed: Mar. 28, 1996

[86] PCT No.: PCT/SE96/00402

§ 371 Date: Dec. 2, 1997

§ 102(e) Date: Dec. 2, 1997

[87] PCT Pub. No.: WO96/29928

PCT Pub. Date: Oct. 3, 1996

[30] Foreign Application Priority Data

Mar. 28, 1995 [SE] Sweden .................................. 9501114

[51] Int. Cl.⁶ ........................................................ A61B 5/0484
[52] U.S. Cl. ................................................................ 600/544
[58] Field of Search ....................................... 600/544, 545

[56] References Cited

FOREIGN PATENT DOCUMENTS

WO87/00745  2/1987  WIPO .
WO91/19453  12/1991  WIPO .

*Primary Examiner*—Scott M. Getzow
*Attorney, Agent, or Firm*—Shapiro and Shapiro

[57] ABSTRACT

The invention relates to a method and a device for determining and monitoring the degree of narcosis in a subject. The determination proceeds as follows. Auditory stimuli are generated by means of a stimulus generator (1). Response signals which signalize the response of the auditory chain to said stimuli are picked up by means of electrodes (4) on the patient's head (3). The response signals are converted by a digitizer into digital response signals. For each digital response signal, an implementation is generated by selecting a portion of the digital response signal. A signal processing means (7) is arranged, by means of which a first and a second mean signal of implementations is formed and by means of which the second mean signal is adapted to the first mean signal for forming an adapted mean signal. Finally, a waveform estimate of the adapted mean signal is formed with the aid of the signal processing means. For monitoring the degree of narcosis, it is possible either to study the actual waveform estimate or to determine and study some suitable parameter, which is dependent on the degree of narcosis, in the waveform estimate.

15 Claims, 5 Drawing Sheets

METHOD AND DEVICE FOR DETERMINING AND MONITORING THE DEGREE OF NARCOSIS IN HUMANS

TECHNICAL FIELD

The present invention relates to the monitoring of a subject's general state of health, more specifically to a method and a device for determining and monitoring the degree of narcosis in a subject according to the preamble to claim 1 and the preamble to claim 10 in the appended claims.

BACKGROUND OF THE INVENTION

In connection with a surgical operation, it is often necessary to lower the patient's degree of consciousness to make it possible to carry out the operation. Therefore, the patient is put under anaesthetic. Anaesthesia in connection with surgical operations, however, is always combined with serious risks for the patient. Thus, the following serious, undesirable states may arise:

1. In spite of anaesthesia, the patient mentally experiences what is going on in the operating theatre. This can be experiences to be very unpleasant and can make the patient suffer mentally.
2. The patient experiences pain but is not able to communicate with those around him. This state is very unpleasant and can make the patient suffer mentally.
3. The patient dies owing to too high a degree of narcosis.

The states 1 and 2 occur owing to too low a degree of narcosis, whereas the state 3 is the result of over-dosing. Apart from the wish to prevent the above-mentioned serious consequences of incorrect dosing, there is a general wish to use as low a degree of narcosis as possible in order to shorten the time of awakening. This yields in a minimum effect on the patient and besides reduces the public nursing expense. Therefore there is a strong wish to be able to accurately determine the degree of narcosis, which is also called anaesthetic depth.

The monitoring of narcosis during surgical operation, however, is still a clinical problem. Modern surgery and the development of new anaesthetics have, if anything, accentuated this problem. Certainly the technical progress in the monitoring of narcosis has made it possible to follow vital parameters such as oxygen saturation, blood pressure, and the concentration of anaesthetic in the exhalation air. These possibilities, however, do not give a direct measure of the patient's anaesthetic depth, but they merely result in a rough picture of the patient's state. Moreover, there is a strong dependence on the type of anaesthetic used and the other drugs used in connection with the operation.

Progress in neurophysiological measuring methods has caused expectations of being able to continuously follow the patient's anaesthetic depth. In recent years, much research has been directed to the measuring of cerebral electric activities during anaesthesia and similar states with a reduced level of consciousness. A general example is the measuring of conventional EEG (electroencephalogram), which has not given any results. However, there have recently been reports on a so-called auditory evoked potential, i.e. an electric stimulus response to auditory stimulation, containing the necessary information. For comparison, it can be mentioned that EEG reflects the system at rest. Auditory evoked potential reflects the level of cerebral activities and is today used routinely for diagnosing hearing disorders by means of a brainstorm audiometer.

A brainstem audiometer registers the variation in voltage that occurs between two electrodes placed on the head when the brainstem and the auditory nerve are activated in acoustic stimulation. The response that is registered by the brainstem audiometer is part of an auditory electric response, AER, which is generated in the auditory chain, i.e. the auditory nerve and different parts of the brain, in acoustic stimulation.

The auditory electric response is usually divided in time as follows. Early responses (0–2 ms), quick responses (2–10 ms), medium-late responses (10–50 ms) and late or slow responses (50–300 ms).

In the range of early responses there is the summed-up action potential from the auditory nerve which is derived from the inner ear and the auditory nerve and which is registered by means of a technique called electrocochleography (EcoG). In the range of quick responses, there is the brainstem response that is generated in the auditory nerve and the brainstem and which consequently is registered by means of a technique called brainstem audiometry. In the range of slow responses, there is the auditory cortical response, which is substantially derived from the auditory part of the cerebral cortex and which is registered by means of a technique called cerebral cortex audiometry. The range of medium-late responses and the earlier part of the range of late or slow responses constitute the part of the auditory electric response that has been found to be the most interesting one to be studied for the purpose of determining the anaesthetic depth. In fact, this part of the auditory electric response is of different appearance at different anaesthetic depths. Besides, the changes are the same no matter what anaesthetic has been used.

For comparison, it can be mentioned that the early and quick responses, i.e. between 0 and 10 ms, change insignificantly during anaesthesia, and that the slow response changes, but its later part is also highly dependent on factors such as attention, sleep and sedatives, and therefore these responses are unreliable.

There is today a known method of measuring the anaesthetic depth by studying responses that are, above all, medium-late, but that can also be included in the range of late responses. The method is carried out by means of a modified brainstem audiometer. This brainstem audiometer is basically made up of three units, a registration unit comprising electrodes, amplifiers, filters and A/D converters; a stimulating unit comprising a signal generator, an amplifier and a sound generator; and a control unit/computer, to which the registration unit and the stimulating unit are connected. The control unit/computer coordinates the generation of sound and the collecting of data and processes the data values collected by means of the electrodes, and then finally presents the results.

The signals that one wants to measure are of the magnitude microvolt, while physiological noise signals from the rest of the brain, from the heart and the muscles can be of the magnitude hundreds of microvolt. Moreover, external noise signals may be present, in the form of electric or magnetic fields from the surrounding electric equipment or in the form of noise in the actual measuring equipment. The external noise signals can either be shielded or filtered off. The physiological noise signals are more difficult to handle. Thanks to the frequency band for the signals that one wants to measure being substantially known, the major part of the noise signals can be filtered off by means of said filters in the registration unit. However, there is a sufficient amount of noise signals in the frequency band for the signal that one wants to measure to make this disappear completely in the noise in the measured signal.

This problem is solved by means of averaging, which means that the signal one wants to measure is estimated by addition and means value calculation of a large number of individual, measured signals. These calculations take place in the control unit/computer. The addition of about one thousand measured signals is in many cases necessary in order to obtain an acceptable curve. By acceptable is meant that the above-mentioned change of the curve depending on the narcosis can be observed.

As mentioned above, the medium-late and late responses are taken into consideration. They are in the range of about 20–80 ms after the generation of the auditory stimulation. By applying the prior-art method for determining the narcosis, it thus takes, theoretically seen, at least 80 s to merely produce an acceptable curve, i.e. 1000 implementations each amounting to 80 ms. However, in practice the time is more than 2 min owing to the fact that the response must die away to a sufficient degree so as to prevent standing-wave ratios and interference phenomena from arising owing to overlapping responses. Certain circuit delays will also arise.

In continuous monitoring of narcosis in real time, quick responses are required. For this reason, one cannot rely on information that is several minutes of age. The above-described prior-art method and device for determining the anaesthetic depth therefore are not applicable in practice.

SUMMARY OF THE INVENTION

One object of the present invention is to provide a method for determining the degree of narcosis in a subject, said method being considerably quicker than the known method, and a corresponding device for carrying out the method.

According to the invention, the subject is achieved by a method having the features as stated in appended claim 1 and a device as defined in claim 10.

A further object of the invention is to provide a method and a device for easily interpreted presentation of the degree of narcosis and the change thereof.

This object is achieved by means of an embodiment of the invention according to claim 7.

BRIEF DESCRIPTION OF THE DRAWING

The invention will now be further described with reference to the accompanying drawing which illustrates an embodiment.

DESCRIPTION OF THE PREFERRED EMBODIMENT

Figure 1:
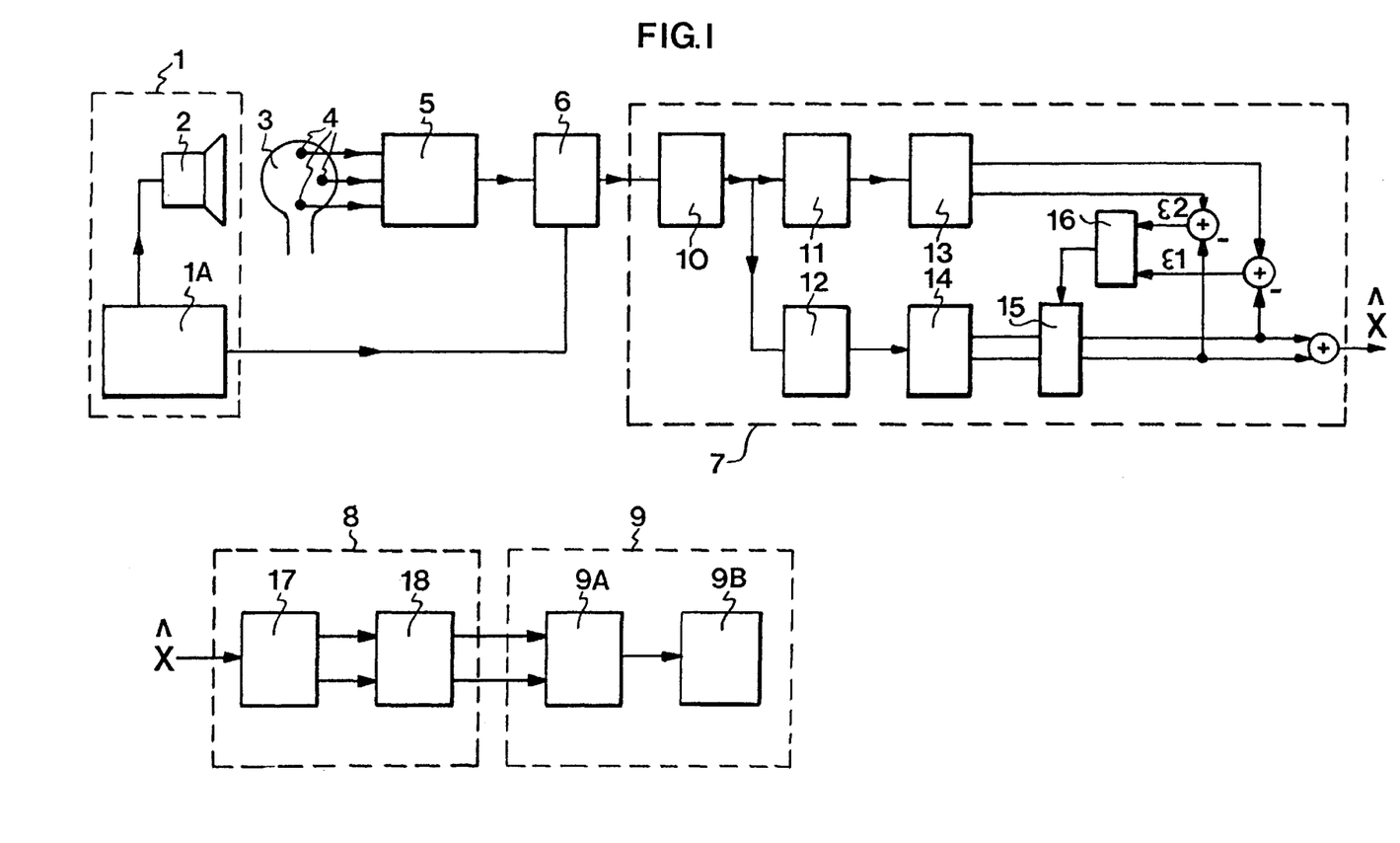
FIG. 1 is a block diagram of an embodiment of a device for determining the degree of narcosis according to the invention.

FIG. 1 shows a preferred embodiment of a device according to the invention. The device is made up as follows. A stimulus generator 1 for generating an auditory stimulus comprises a circuit 1A for generating a short electric signal and an electroacoustic converter 2 for converting the electric signal into an acoustic signal, such as an earphone. Electrodes 4 are arranged on a patient's head 3 and are connected to a digitiser 5 comprising an amplifier and an A/D converter. The output of the digitiser 5 is connected to a cutting circuit 6, which cuts out part of a signal supplied by the digitiser 5. Also the stimulus generator 1 is connected to the cutting circuit 6 for triggering thereof. The output of the cutting circuit 6 is connected to a first signal processing unit 7, which is indicated by a dashed line and which below is called waveform estimator 7. The shown, various partial circuits of the waveform estimator 7 will be described below. The output of the waveform estimator 7 is connected to a second signal processing unit 8, which is indicated by a dashed line and which in the following is called amplitude/latency estimator 8. The shown parts of the estimator 8 will be described below.

Finally, the device also comprises a presentation unit 9 connected to the amplitude/latency estimator 8 and comprising a preparing circuit 9A for preparing information for easily interpreted pictures and a display device, and LED display or the like, for presenting the pictures.

A preferred embodiment of the inventive method will now be described, in combination with a more detailed description of the device shown in FIG. 1 and the function thereof. The circuit 1A of the stimulus generator 1 generates at regular intervals an electric signal, which is fed to the converter 2. Suitable generating frequencies are stated below under the heading "Tests". The converter 2 emits an audible signal, which is perceived by the patient 3 and generates electric response signals in the patient's various organs for registering sound. The audible signal should be short, for reasons that will be described below, and in the preferred embodiment of the invention, a click sound is generated. The electric response signals are perceived by means of the electrodes 4 on the head 3, are amplified, filtered and A/D converted in the digitiser 5, which consequently supplies a digital response signal. Bandpass-type filtering is involved, where a priori knowledge of the frequency content of the response signals is used. The digitising occurs continuously, but when determining the anaesthetic depth, a portion of the response which generally arises 20–80 ms after the auditory stimulation will be taken into consideration, as has been described above. An about 100-ms-long portion of the digital signal is therefore cut out by means of the cutting circuit 6, starting when the cutting circuit 6 is triggered by the stimulus generator 1. At a preferred sampling frequency, in the digitiser 5, of 2 kHz, a vector having about 200 samples is obtained. This vector is below called implementation.

External noise signals are substantially filtered off in the digitiser 5, and the implementation is, also in respect of frequency, band-restricted to about the band in which the information of interest is available. The implementation is fed to the waveform estimator 7. With the aid of the waveform estimator 7, the desired information is estimated, which in the implementation is concealed in noise signals having a many times greater amplitude. The technique of generating this estimate $\hat{\chi}$, which is a keystone of the invention, will be further described below. The estimated waveform $\hat{\chi}$ is fed to the amplitude/latency estimator 8. With the aid of the amplitude/latency estimator 8, one or more parameters in the estimated waveform $\hat{\chi}$ are determined, which are adequate for determining the degree of narcosis. In this embodiment, two parameters are determined, viz. amplitude and latency of the estimated waveform, and more specifically, amplitude and latency in a certain curve point on the waveform. This point is a local minimum, which is designated Nb in this technical field and which is obvious when the patient is both awake and under heavy anaesthetic. The result is presented on the display device 9 in an easily interpreted manner, such that a user can very quickly perceive the patient's state.

Let us now study the generation of the waveform estimate $\hat{\chi}$ from the implementation. First, it is decided in step 31 in FIG. 3 whether the implementation must be rejected or not. If the perceived response signal contains noise of great amplitude, it will be cut in the digitising and give an implementation which is not usable in the continued signal processing. It is a complex problem to decide which implementations should be rejected. In a preferred embodiment of the invention, use is made of an adaptive manner to make it possible to trace the true amplitude properties of the implementation when the patient is awake and under anaesthetic. Known techniques of deciding upon the relevance of implementations utilise fixed limits which are too rigid and which in these contexts, owing to the difficult noise conditions that prevail, would often include not usable implementations, resulting in an inferior estimate, and reject usable, relevant implementation, which would result in a greater time delay than necessary. The method according to the preferred embodiment of the invention is based on a ratio of the greatest signal amplitude to the power of the signal. This ratio will be small when the signal contains A/D saturated samples, but also when it contains amplifier-cut samples. By tracing the normal ratio of the implementations, it will be possible to reject an abnormal implementation of its ratio is considerably lower than the normal.

Figure 2A:
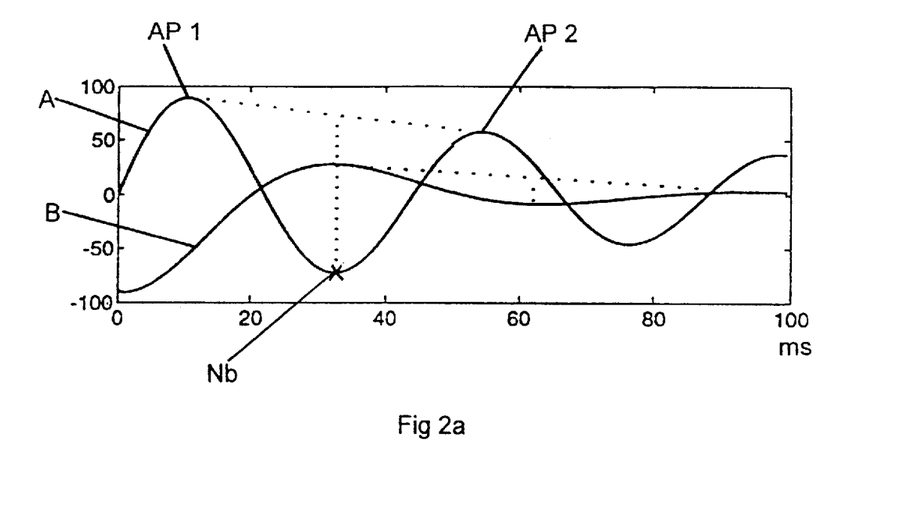
FIGS. 2a–e show various estimates of the measured signal.
Figure 2B:
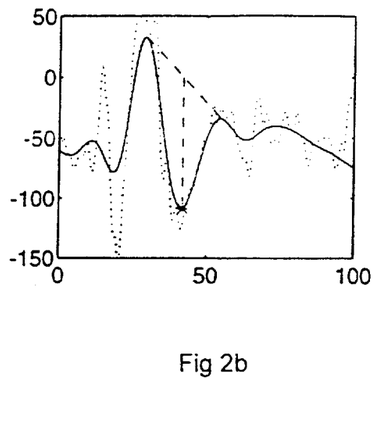

If the implementation is not rejected, two different averagings occur in parallel in the next step, step 32 in FIG. 2. On the one hand, a short mean is determined with the aid of a first signal averager 11, and, on the other hand, a long mean is determined with the aid of a second signal averager 12. The forming of the long means corresponds to conventional averaging and gives an estimate of relatively low variance, i.e. with little noise. However, since this averaging takes too long to make it possible to use the estimate for practical monitoring a narcosis, a method of obtaining more quickly a usable result is provided according to the invention. This is carried out in step 34, which comprises partial steps as illustrated in the flow diagram in FIG. 4. To shorten the estimation time, use is made, according to this embodiment of the invention, of the short mean, is which the long mean is adapted. The adaptation is carried out as follows. The short means is filtered in two frequency bands, which substantially divide the frequency content into two portions, with the aid of bandpass filters in a first set of filters 13, step 41 in FIG. 4. The long mean is filtered correspondingly by means of a second set of filters 14, step 41. The signals representing the filtered long mean are filtered a second time in an adaptation filter 15. The adaptation filter 15 is adaptive and optimal and its coefficients are determined by minimising the residual energy between the output signals from the adaptation filter 15 and the signals corresponding to the filtered short mean. This mean, as will be described below in more detail, that the auto-correlation for the output signals from the filter 15 and the cross-correlation between these and the output signals from the set of filters 13 are determined, step 42, whereupon these correlations are used to determine the coefficients in the adaptation filter 15, step 43. Steps 42 and 43 are carried out by means of a coefficient generator 16. The output signals from the adaptation filter 15 are joined, for instance, summed up, and form the waveform estimate $\hat{\chi}$, step 44.

Figure 4:
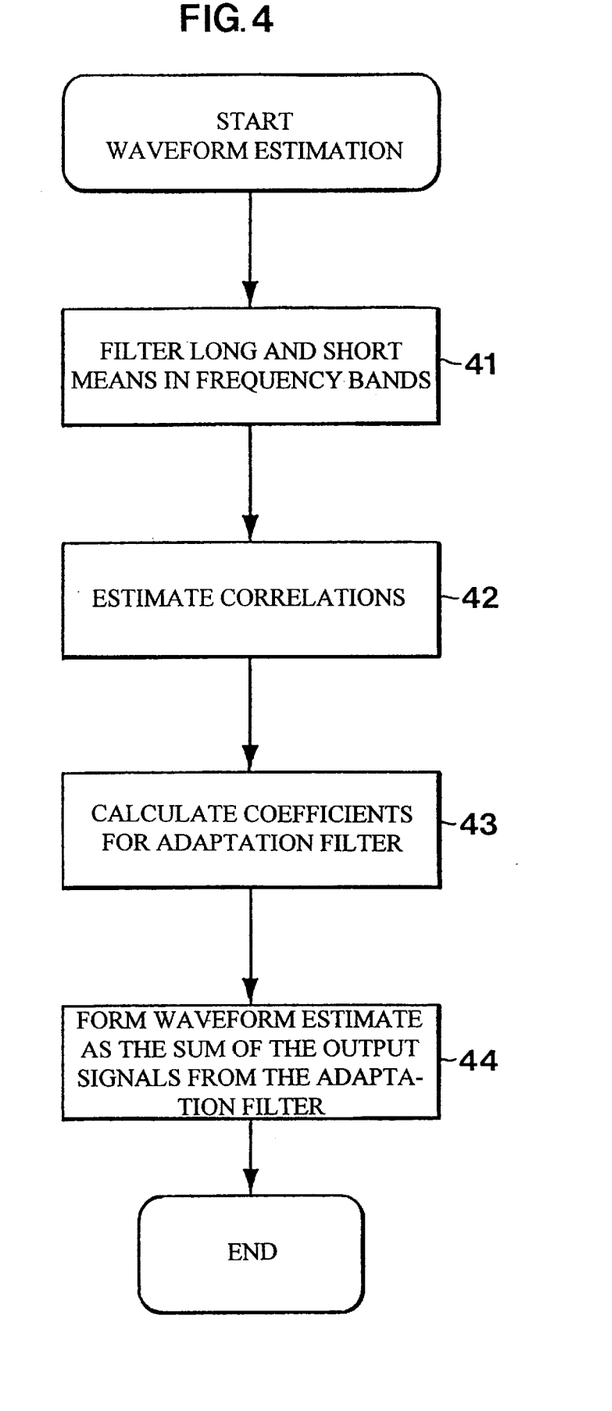
FIG. 4 is a flow diagram of partial steps in one of the steps in FIG. 3.

It is advantageous to filter, according to this preferred embodiment of the invention, and, thus, divide the mean signals into frequency bands, preferably an upper and a lower, since in this manner a further cancellation of noise signals takes place, which yields a higher signal-to-noise ratio SNR. When a band filtering is also carried out in the adaptive adaptation filter 15, the division is used in an advantageous manner to further improve the SNR. In the adaptation filter 15, a further limitation is carried out, viz. in time. Thus, the adaptation filter 15 cuts away information which is earlier than 20 ms and later than 80 ms after the stimuli generation.

Now follows a mathematical description of the criterion for selecting implementations and for determining the waveform estimate $\hat{\chi}$ from the implementation.

The criterion for determining whether an implementation should be rejected or not is:

$$Cr = \frac{max|y_{in}(n)|}{\frac{1}{M}\sum_{n=1}^{M} y_{in}^2(n)} \quad (1)$$

In equation (1), $y_{in}(n)$ represents the implementation that is fed to the circuit 10 and M the number of samples in the implementation. If the implementation is accepted, i.e. Cr>0.6 Crm, the value Crm is updated, Crm being a median of previously accepted Cr values.

The averaging occurs recursively according to the following equation:

$$y^{(k)}_{avg} = \alpha y^{(k-1)}_{avg} + (1-\alpha) y^{(k)}_{in}. \quad (2)$$

In equation (2), $y^{(k)}_{avg}$ represents the resultant mean, which is a vector of the length M, $\alpha$ is the control parameter and k is an index for updating the implementation. The effective length of the averaging is approximately:

$$N \sim \frac{2}{1-\alpha}. \quad (3)$$

The averaging takes place with two different lengths, $N_1$ and $N_s$, which give the long and the short means, respectively.

The first set of filters 13 and the second set of filters 14 are in the preferred embodiment of the invention implemented as FIR filters. Since the interesting portion of the signal begins at about 20–30 ms after stimulus, the impulsory response for these filters should not be much longer. At the sampling frequency 20 Hz, this is equivalent to 40–60 filter coefficients.

The means are filtered in the two frequency bands. The filtration can be described as follows:

$$y^{(kk)}_{filt}(n) = \sum_{l=1}^{L_f} f(l) y^{(kk)}_{avg}(n-1), n = 1 \ldots M. \quad (4)$$

In equation (4), f(1) represents filter coefficients, $L_f$ filter length and kk index for updating of amplitude and latency, see step 33 in FIG. 3. This updating does not occur for every new implementation, for reasons that will be explained below. Zeros are added in the beginning of $Y_{avg}$, thereby permitting indexing outside $Y_{avg}$.

The number of multiplications is bisected by using the symmetry. The resultant signals of the filtered long means $Y_{filt1}$ are adapted to the filtered short means $Y_{filts}$. This means that the mean residual energy $\epsilon 1$, $\beta 2$, see FIG. 1, for the signals in each band is minimised, which yields:

$$\min_{b} E\left(y_{filts}(n) - \sum_{l=1}^{L} b(l) y_{filts}(n-l)\right)^2, n = n_{start} \ldots n_{stop}. \quad (5)$$

In equation (5), $n_{start}$ and $n_{stop}$ represent start and stop index for the curve adaptation, i.e. the limitation in time, and b represents the coefficients of the adaptation filter 15. The minimising of equation (5) results in the Wiener-Hopf equations:

$$\sum_{l=0}^{L-1} b(l)n(m-l) = r_{s1}(m), m = 0 \ldots L-1, \quad (6)$$

In equation (6), $r_1(m)$ represents the auto-correlation function of $y_{filt1}$, and $r_{s1}(m)$ is the cross-correlation function of $y_{filts}$ and $y_{filt1}$. The cross-correlation function codes are estimated for each filtering band as time means as follows:

$$P_1(m) = \frac{1}{M_1} \sum_{n=1}^{M_i-|m|} y_{filt1}(n)y_{filt1}(n+1), m = 0 \ldots L-1, \quad (7)$$

and $$P_{a1}(m) = \frac{1}{M_1} \sum_{n=1}^{M_1-|m|} y_{filt1}(n)y_{filts}(n+1), m = 0 \ldots L- \quad (8)$$

In equations (7) and (8) $M_1 = n_{stop} - n_{start} + 1$. By using the correlation estimates in equations (7) and (8), coefficients b are obtained for an optimal adaptation filter (15) by solving equation (6). Equation (6) is quickly solved, for instance, by means of a Levinson algorithm. The estimated waveform finally results from:

$$\hat{\chi}^{(kk)}(n) \approx \sum_{j=1}^{2} \left[ \sum_{i=1}^{L} b_j(l)y_{filt(j)}(n-1) \right], n = 1 \ldots M. \quad (10)$$

In equation (10), $b_1$ is the filter that is derived from the lower frequency band and $b_2$ is the filter that is derived from the higher frequency band.

The operation of the second signal processing unit 8 will be described in more detail below. The waveform estimate $\hat{\chi}$ which reaches the input of the unit 8 can, when the patient is awake, basically be described by means of the curve designated A and shown in FIG. 2a. According to a preferred embodiment, two properties of a given point on curve A are studied, curve A being designated Nb. Nb is a common designation among experts. The studied properties are the amplitude of the curve in point Nb, expressed as the vertical distance from a straight line A1, between the closest peaks AP1 and AP2 on each side of Nb, to Nb. The second property is the latency in point Nb, i.e. the time that has lapsed after generation of the auditory stimulus. In the example shown, the amplitude is −150 and the latency is 32 ms. The latency when awake is mostly between 30 and 40 ms. With an increasing degree of narcosis, the latency increases, whereas the amplitude decreases. The second curve from B in FIG. 2a is a fundamental example of the possible appearance of the curve form during anaesthesia of average depth. In this case, the latency is about 62 ms and the amplitude is −20. The absolute value of the amplitude is of less interest since this can be selected through the amplification of the system etc. All the more interesting is the change of amplitude that follows with a varying degree of narcosis.

To be able to determine the degree of narcosis, first an initiation is carried out, in which a waveform estimate based on a 2-min-long averaging is generated. This waveform estimate is of low variance and gives good opportunities of determining relevant output values of amplitude and latency. An actual example of an initial waveform estimate is shown in FIG. 2b. The determination of the output values of amplitude and latency is based on a priori knowledge of where the point Nb is usually available when awake. This a priori knowledge in combination with the good estimate results in the fact that a local minimum that is assumed to be Nb is, most certainly, correctly selected.

Figure 2C:
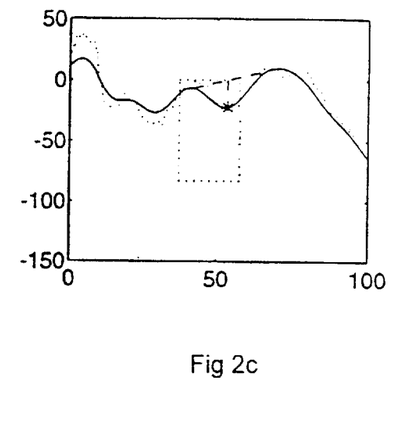

In view of the output values, a window with defined upper and lower limits for both latency and amplitude is determined, see the square F indicated by dotted lines in FIG. 2c. This window marks the area that is scanned next time the point Nb and the values of amplitude and latency in this point should be determined. The limits of the window F are updated for each new determination. The position in time of point Nb is determined by determining a local minimum within the window. For checking the relevance in the determined point, a comparison is made with the preceding position. The difference should not be too great. The latency is equal to the position in time of point Nb. For determining the amplitude, the closest local maxima are determined on both sides of Nb, a straight line between these local maxima is determined, and the vertical distance from the line to point Nb is determined. This vertical distance constitutes the amplitude. The determination of amplitude and latency goes on continuously and can have the appearance as shown, for instance, in FIGS. 2d and 2e, respectively. In these Figures, the full lines indicate the estimates of latency and amplitude, respectively, after filtration thereof by means of a median filter, which is designated 18 in FIG. 1. The dotted waveforms indicate the estimates before the median filter 18. Although the median filtration introduces a delay, it yields considerably more robust estimations of amplitude and latency and therefore is preferred.

Below follows a mathematical description of the operation of the amplitude/latency estimator 8. The search for minima and maxima is based on the difference:

$$d\hat{x}(n) = \hat{x}(n+1) - \hat{x}(n). \quad (11)$$

The minimum has been found when the criteria:

$$d\hat{x}(n_0) < 0$$
$$d\hat{x}(n_0+1) \geq 0 \quad (12)$$

are satisfied. In order to avoid estimation of a small, incorrect minimum caused by interference, limits are introduced for the difference both in latency and in amplitude, which results in the criteria:

$$d\hat{x}(n-\Delta) < -\epsilon$$
$$d\hat{x}(n+\Delta+1) \geq \epsilon \quad (13)$$

By this is meant that at certain distances $\pm\Delta$ from the minimum, the difference must still be below $-\epsilon$ and above $\epsilon$. By using these criteria, false minima are excluded, such as very flat and very pointed minima. However, the true minimum is detected.

Subsequently, the amplitude is calculated by using maxima on each side of the minimum. These maxima are not allowed to be too close to the minimum for the purpose of excluding noise maxima, and therefore the search is carried out from $n_{min}-\Delta$ for $n_{left}$ and $n_{min}+\Delta$ for $n_{right}$. An equivalent criterion like the one used to find the minimum is used for detecting maxima, with the difference that the relational operators in equations (12), (13) are exchanged. If no maximum is found on one side, the distance is selected as far from the minimum as the maximum is positioned on the other side. If no maximum is found on any of the sides, maxima are selected as the points that are available at a predetermined distance from the initial and final points.

It is necessary to restrict the possibility of estimating amplitude and latency on the basis of an incorrect minimum.

These limits depend on the individual as well as on the condition. For this reason, the limits are adaptive, Let $\text{Ref}^{(k_2)}$ be a vector having two elements containing the reference values for amplitude and latency that are used to calculate the limits. The updating of this vector is carried out as follows:

$$\text{Ref}^{(k_2)} = \alpha_{a1}\text{Ref}^{(k_2-1)} + (1-\alpha_{a1})[\text{AMP LAT}]^T \quad (14)$$

wherein AMP and LAT are the median for the last amplitude and latency estimates of Nb, and they are also the final estimate presented to the user. The limits for amplitude and latency are selected as deviations from $\text{Ref}^{(k_2)}$. The permitted amplitude range and latency interval are controlled by a parameter $\text{Diff}^{(k_2)}$, where the first element in $\text{Diff}^{(k_2)}$ is the amplitude deviation and the second element is the latency deviation. The latter remains fixed to a given value from one updating to the next, while the amplitude range parameter is calculated as follows:

$$\text{Diff}^{(k_2)}(1) = b\text{Ref}^{(k_2)}(1) + (1-b)\text{ref}_{amp} \quad (15)$$

The initial and final search limits are then obtained from $$\text{Beg}^{(k_2)} = \text{Ref}^{(k_2)} - \text{Diff}^{(k_2)}$$

$$\text{End}^{(k_2)} = \text{Ref}^{(k_2)} + \text{Diff}^{(k_2)}. \quad (16)$$

If the estimated Nb has a latency that is within the limits in equation (16), the amplitude is calculated. If the amplitude is within the amplitude limits, the estimates are accepted.

When the estimates of amplitude and latency have been determined, it remains to present them in such a manner that the user, such as the operation team, can quickly read the patient's state. For instance, curves similar to those in FIGS. 2a and 2e can be shown. Such a composed picture can be formed and shown by means of the presentation unit 9, the estimating circuit 9A being used to calculate the degree of narcosis and prepare picture data.

The device according to the invention operates at different speeds in different parts. Thus, auditory stimuli are generated at a time interval $t_{stim}$, or at the frequency $f_{stim}=1/t_{stim}$, the A/D converter operates at the sampling frequency $f_s$, a new implementation is generated, i.e. k is adjusted upwards, for each stimulus, and the estimates of latency and amplitude are calculated at the frequency $f_{stim}/U$, i.e. the amplitude and latency estimates are updated more seldom than in every new implementation. This depends on the fact that the amplitude and the latency change to a comparatively small extent between two implementations, and therefore the many steps that remain after averaging need not be carried out very often.

Tests

In order to illustrate how the invention functions in practice, a practical test will be described below.

In one test, the following values were used:

$t_{stim}=119$ ms;
$f_s=2$ kHz;
length of one implementation=100 ms, i.e. M-200;
$N_s=250$;
$N_1=1000$;
U=31;

Moreover, FIR filters of the length 60 were used in the sets of filters 13, 14, and adaptive FIR filters of the length 20 were used as the adaptation filter 15. The adaptive FIR filters were set so as to result in a limitation in time for samples Nos 60–140, i.e. 30–70 ms. The median filter 18 was of the length 15.

This resulted in the initial estimate as shown in FIG. 2b, and an estimate after 6.28 min are shown in FIG. 2c. This estimate indicates that the latency has increased significantly and the amplitude has decreased significantly since the beginning of the test. At this point of time, the patient was under anaesthetic, which will also be the conclusion of the estimate.

The following Table shows the patient's degree of narcosis, conventionally estimated, during the test, and the course of events. The Table should be compared with FIGS. 2d and 2e, which illustrate estimates of latency and amplitude during the test.

TABLE

| Minutes | State |
|---------|-------|
| 0 | Patient awake |
| 3 | 1/2 narcosis |
| 7 | 3/4 narcosis |
| 10 | 1/1 narcosis |
| 14 | 1/1 narcosis, no surgery |
| 17 | Surgery is begun |
| 21 | Surgery |
| 24 | Surgery is completed |
| 28 | End of surgery |
| 31 | Superficial narcosis |
| 34 | Answer when spoken to |

Figure 2D:
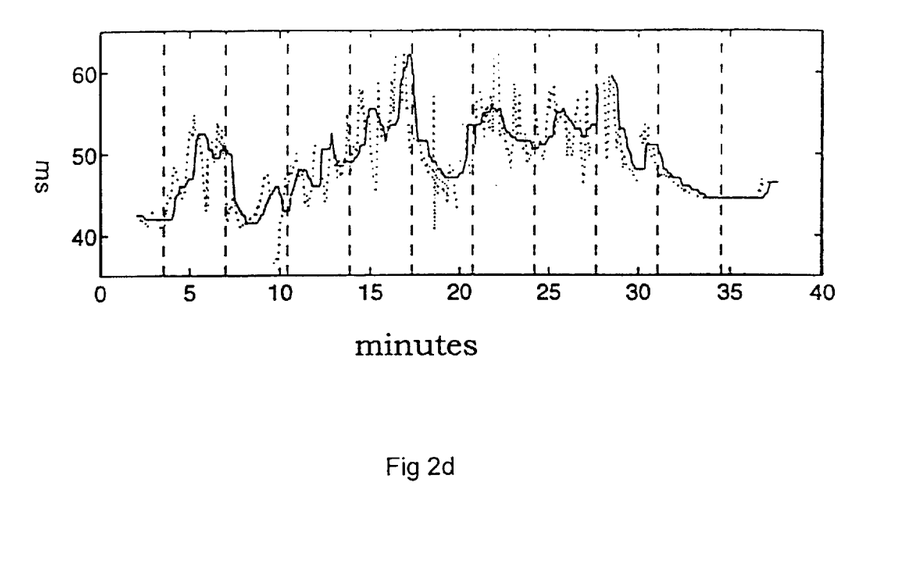
Figure 2E:
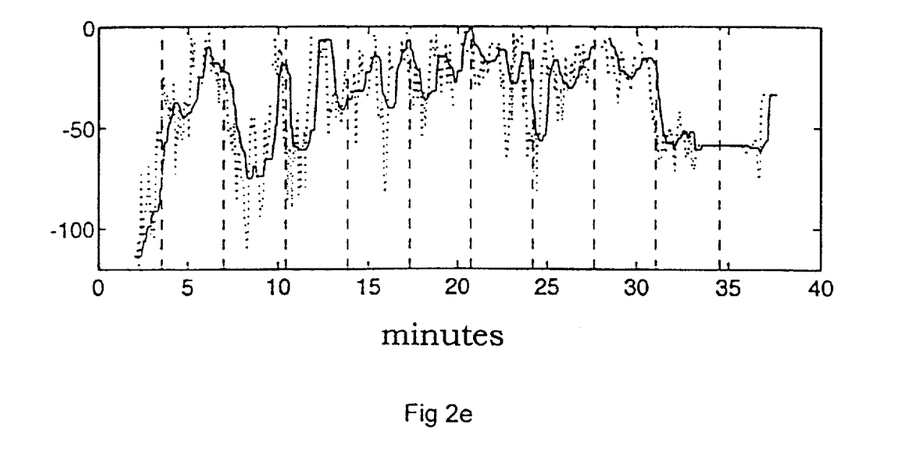
Figure 3:
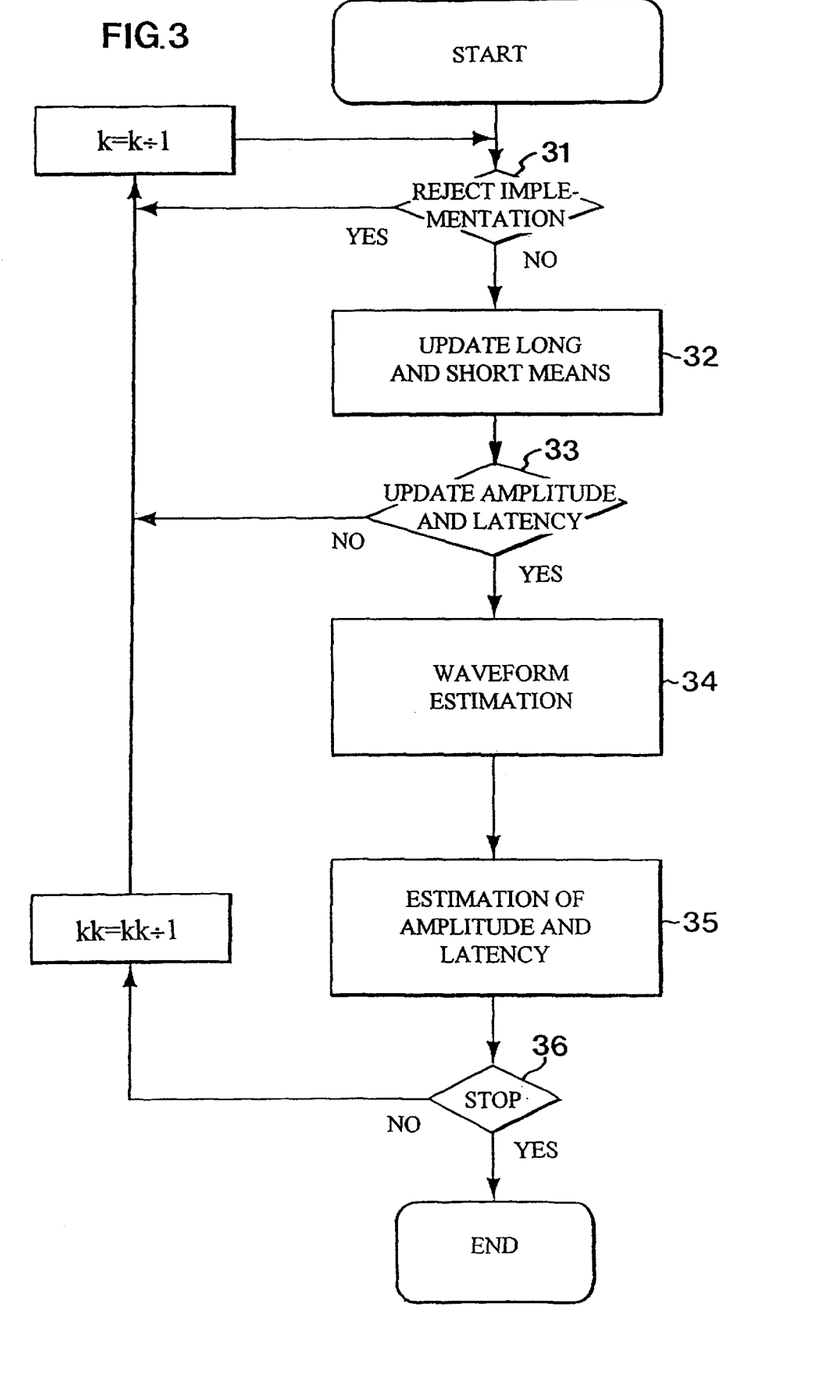
FIG. 3 is a flow diagram of an embodiment of the method according to the invention.

It should be noted how the latency increases and the amplitude decreases as the narcosis becomes deeper. Also note the marked change that occurs after 17 min when the surgical operation is begun.

The above-described, preferred embodiment of the invention yields a significant result so quickly that it is usable in practical contexts. The values of filter lengths etc. which are stated in the above test, should be studied as an example of the delay in the device. The delay is created substantially in two positions, on the one hand in the averaging and, on the other hand, in the median filtering. Thanks to the long means being adapted to the short (250 implementations), the averaging contributes with about 30 s only. The median filter (length 15) causes a delay of about 25 s. Thus, a total delay of 55 s is obtained. Such a delay is acceptable and less than half the delay in the known device. As will be evident from the following, the median filter is not absolutely necessary, whereby the result is, of course, produced still more quickly.

Alternative Embodiments

The above-described, preferred embodiments of the method and the device according to the invention have been described for the purpose of exemplification, and many modifications are feasible within the scope of the invention as defined in the claims.

Auditory stimuli are generated regularly as described above. The frequency can be varied within a wide range, which is theoretically limited upwardly by the length of the response that one wants to study, and is practically limited by the possibilities of suppressing the remaining portions of the response. The frequency is limited downwardly by the maximum delay permitted in the system. Moreover, it is not necessary to generate stimuli regularly, but a more irregular or random generation can be preferred.

The lamination of implementations is not quite necessary, but if it is carried out, it may of course be carried out in many different ways, for instance, in the manner that is so far most used and means that the implementation is rejected if a certain number of samples are too much modulated. However, the new method described above is the one that gives optimum results.

The averaging need not be recursive implementation by implementation but can take place in blocks, in which case, for instance, a number of implementations ($N_s$ and $N_1$, respectively) are stored and averaged. Moreover, instead the median can be determined, in which case also a sorting of the stored implementation is necessary. In these alternative embodiments, there is a need of extra storage capacity for storing the great number of implementations, and extra data processing capacity for handling and updating the memory for each new implementation. These and other similar alternatives are included in this application within the term averaging.

The lengths of the averagings can be varied within a fairly side range depending on application and depending on which parameter is to be determined, but if, in the monitoring of narcosis, one wants to obtain a result which is practically applicable to continuous monitoring in real time, approximately 600 implementations would constitute an upper limit for the short averaging. A lower limit would be found in approximately 100 implementations, but this is fairly dependent on the SNR in the implementations.

The filtering which is carried out after averaging can be performed in one or more frequency bands. The selected division into two bands, however, is preferred, since a more satisfactory suppression of noise is then obtained as compared with filtering in a single band, and at the same time the problem that increases with an increasing number of bands is substantially obviated. This problem resides in the fact that a narrower band width is associated with a longer settling time, which is not desirable in view of the relatively limited length of each implementation. In practice, it is also possible to use three bands, whereas more bands result in noticeable drawbacks. This reasoning is also applicable to the adaptation filter.

The filters for filtering the output signals from the averaging can also be IIR filters or filters of some other suitable type. The adaptation filter 15 can also be some other suitable type of filter.

When determining filter coefficients for the adaptation filter, any suitable method can be used, but a loss criterion as a function of the residuals would probably be preferred.

The estimated waveform that is obtained with the aid of the first signal processing unit constitutes the base for determining the degree of narcosis and instead of determining amplitude and latency for Nb or some other point on the waveform, it is possible to determine, for example, some other parameter, such as the frequency content (by transforming the waveform to the frequency plane and showing the frequency content) since this changes with the degree of narcosis, or quite simply show the estimated waveform itself.

It should also be pointed out that the initiation is not absolutely necessary and that the determination of the degree of narcosis can be begun when the patient is already anaesthetised.

We claim:

1. A method for determining the degree of narcosis in a subject, comprising the steps of:
    a) generating auditory stimuli;
    b) detecting response signals, which signalise the responses of the auditory chain to said stimuli;
    c) converting the response signals into digital response signals;
    d) generating for each digital response signal an implementation by selecting a portion of the digital response signal;
characterised by the steps of:
    e) forming a first mean signal of implementations;
    f) forming a second mean signal of implementations;
    g) adapting the second mean signal to the first mean signal so as to form an adapted mean signal; and
    h) forming a waveform estimate by means of the adapted mean signal.

2. The method as claimed in claim 1, characterised by the steps of:
    i) forming the first mean signal as a first recursive mean of the implementations, the length of the recursion being $N_s$; and
    j) forming the second mean signal as a second recursive mean of the implementations, the length of the recursion being $N_1$ and $N_2 > N_s$.

3. The method as claimed in claim 1, characterised in that the step g) also comprises the steps of:
    k) filtering the first mean signal in a number BANT of different frequency bands for generating BANT first partial signals;
    l) filtering the second mean signal in BANT different frequency bands for generating BANT second partial signals; and
    m) adapting said second partial signals to said first partial signals for generating BANT adapted partial signals, which constitute the adapted mean signal.

4. The method as claimed in claim 3, characterised by step m) comprising the step of:
    filtering said second partial signals by means of optimal adaptive filters, one for each frequency band, which comprises the determining of the coefficients of the adaptive filters, such that the residual energy of the adapted partial signals and the first partial signals in each frequency band is minimised, the output signals from the adaptive filters constituting the adapted partial signals.

5. The method as claimed in claim 1, characterised by the step of:
    n) determining at least one parameter of the waveform estimate, said parameter changing according to the degree of narcosis in a significant manner.

6. The method as claimed in claim 5, characterised in that step n) comprises the locating of a given curve point on the waveform estimate, said curve point constituting a local extreme value, and the determining of said parameter or parameters for the curve point.

7. The method as claimed in claim 6, characterised by the step of presenting to a user estimates of said parameter or parameters; and in that said parameter or parameters comprise latency, defined as the time that has lapsed from the generation of an auditory stimulus until the curve point arose in the response from the auditory chain, and amplitude, relative to a reference level, in the curve point.

8. The method as claimed in claim 1, characterised by step d) comprising the step of checking that each implementation satisfies a given criterion for useable implementation and otherwise rejecting it.

9. The method as claimed in claim 8, characterised in that the criterion is that a ratio of the greatest amplitude of the implementation to the average power of the implementation should be within a comparison range.

10. A device for determining the degree of narcosis in a subject, comprising a means (1) for generating auditory stimuli; an intercepting means (4) for picking up electric response signals, which are generated in the auditory chain in response to said auditory stimuli; a digitiser (5) connected to the intercepting means an adapted to digitise the response signals; and a selecting means (6, 10) connected to the digitiser and adapted to select a portion of each digitised response signal, said portion constituting an implementation, characterised by a first signal processing unit (7) connected to the selecting means and adapted to generate a waveform estimate, the firs signal processing unit comprising a means (11) for forming a first mean signal of implementations, a means (12) for forming a second mean signal of implementations and an adaptation means (13, 14, 15, 16) for adapting the second mean signal to the first mean signal and for generating the waveform estimate by means of the adapted mean signal.

11. The device as claimed in claim 10, characterised in that the adaptation means (13, 14, 15, 16) comprises a first set of filters (13) for filtering the first mean signal in a number BANT, BANT≧1, of different frequency bands; a second set of filters (14) for filtering the second mean signal in BANT different frequency bands; and a third set of filters (15, 16) for adapting the BANT output signals from the second set of filters to the BANT output signals from the first set of filters.

12. The device as claimed in claim 11, characterised in that the third set of filters (15, 16) is adapted to filter the output signals from the second set of filters and comprises BANT adaptive filters (15) and a coefficient generator (16) for such determination of the coefficients of the adaptive filters that the residual energy of the output signals from the third set of filters and the output signals form the first set of filters is minimised in each frequency and; and that the adaptation means further comprises a means for uniting the output signals from the third set of filters in order to form the waveform estimate.

13. The device as claimed in claim 10, characterised by a second signal processing unit (8) connected to the first signal processing unit and adapted to generate one or more parameters which signalise the degree of narcosis.

14. The device as claimed in claim 13, characterised in that said one or more parameters comprise latency and amplitude in a selected point on the waveform estimate.

15. The device as claimed in claim 10, characterised in that the means (11) for forming a first mean signal is adapted to form a first recursive mean of the implementation, the length of the recursion being $N_s$; and that the means (12) for forming a second mean signal is adapted to form a second recursive mean of the implementations, the length of the recursion being $N_1$ and $N_1 > N_s$.

* * * * *